US00PP16627P2

(12) United States Plant Patent
Talmadge

(10) Patent No.: US PP16,627 P2
(45) Date of Patent: Jun. 13, 2006

(54) ***FELICIA* PLANT NAMED 'BALPINPERI'**

(50) Latin Name: *Felicia amelloides*
Varietal Denomination: Balpinperi

(75) Inventor: Paul A. Talmadge, Guadalupe, CA (US)

(73) Assignee: Ball Horticultural Company, West Chicago, IL (US)

( * ) Notice: Subject to any disclaimer, the term of this patent is extended or adjusted under 35 U.S.C. 154(b) by 96 days.

(21) Appl. No.: 11/016,289

(22) Filed: Dec. 17, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Felicia* plant named 'Balpinperi' characterized by its single inflorescence form with blue-colored ray florets, yellow-colored disc florets, freely branching character, dark green-colored foliage, bushy type growth habit, and earliness to flower.

1 Drawing Sheet

Latin name of the genus and species of plant claimed: *Felicia amelloides*.
Variety denomination: 'Balpinperi'.

BACKGROUND OF THE INVENTION

The present invention relates to a new and distinct cultivar of *Felicia* plant botanically known as *Felicia amelloides* and hereinafter referred to by the cultivar name 'Balpinperi'.

The new *Felicia* originated in a controlled breeding program in Guadalupe, Calif. during summer 2001. The objective of the breeding program was the development of *Felicia* cultivars that are freely branching, have a compact and upright growth habit, are freely flowering, and are early to flower.

The female parent of the new cultivar was an unnamed commercial *Felicia amelloides* variety, not patented, characterized by its small white-colored flowers, medium green-colored foliage, and late flowering time. The male parent of the new cultivar was a proprietary breeding selection designated 12777, characterized by its light blue-colored flowers, light green-colored leaves, late flowering time, and moderate branching habit. Seed from the above stated cross-pollination was germinated and grown to maturity. One plant within the progeny was discovered and selected by the inventor during autumn 2002 in a controlled environment at Guadalupe, Calif.

Asexual reproduction of the new cultivar by terminal stem cuttings since autumn 2002 at Guadalupe, Calif. and West Chicago, Ill. has demonstrated that the new cultivar reproduces true to type, with all the characteristics as herein described, firmly fixed and retained through successive generations of such asexual propagation.

SUMMARY OF THE INVENTION

The following characteristics of the new cultivar have been repeatedly observed and can be used to distinguish 'Balpinperi' as a new and unique cultivar of *Felicia* plant:

1. Single inflorescence form.
2. Blue-colored ray florets and yellow-colored disc florets.
3. Dark green-colored foliage.

4. Freely branching character.
5. Bushy type growth habit.
6. Earliness of flowering.

Plants of the new cultivar differ from plants of the female parent primarily in flower color and flowering time and from the made parent primarily in foliage color, branching habit, and flowering time.

Plants of the new cultivar are most similar to the cultivar Cape Town Blue, not patented. However, in side-by-side comparisons, plants of the new cultivar differ from plants of 'Cape Town Blue' in the following characteristics:

1. Foliage of the new cultivar is shorter than the foliage of 'Cape Town Blue'.
2. Plants of the new cultivar have darker foliage than plants of 'Cape Town Blue'.
3. Plants of the new cultivar flower much earlier than plants of 'Cape Town Blue'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which more accurately describe the colors of the new cultivar. The plants were grown in 10 cm pots for 8 weeks in a greenhouse at West Chicago, Ill.

DETAILED BOTANICAL DESCRIPTION

Figure 1:
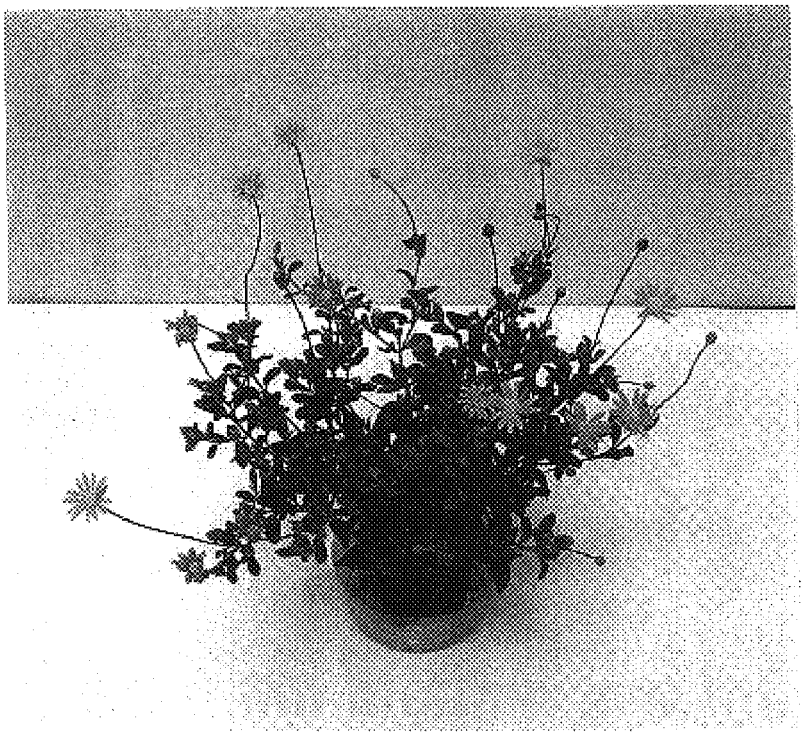
FIG. 1 illustrates a side view of the overall growth and flowering habit of the new cultivar with one plant per pot.
Figure 2:
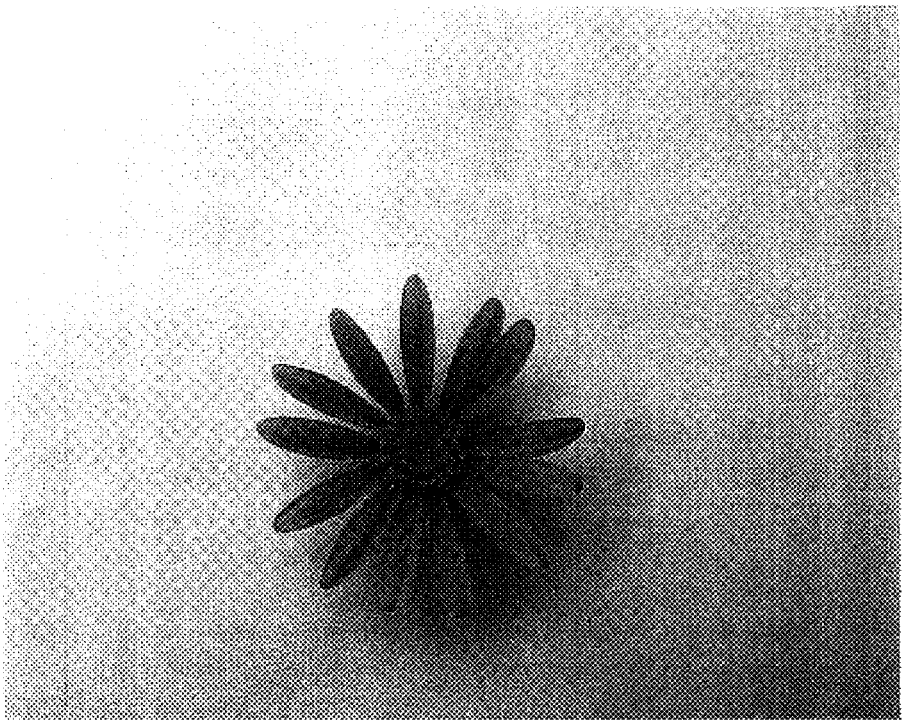
FIG. 2 illustrates a close-up view of an individual flower of the new cultivar.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004 between 1:00 and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soil-less growth medium. Greenhouse temperatures were maintained at approximately 65°–78° F. (18°–25° C.) during the day and approximately 50°–60° F. (10°–15° C.) during the night. Greenhouse light levels were maintained at 6,000 to 9,000 footcandles during the day.

Botanical classification: *Felicia amelloides* cultivar Balpinperi.

Parentage:

*Male parent.*—Unnamed commercial *Felicia amelloides* variety, not patented.

*Female parent.*—Proprietary *Felicia amelloides* selection designated 12777, not patented.

Propagation:

*Type cutting.*—Terminal stem.

*Time to initiate roots.*—Approximately 7 to 10 days.

*Time to produce a rooted cutting.*—Approximately 14 to 21 days.

*Root description.*—Fine, fibrous.

*Rooting habit.*—Freely branching.

Plant description:

*Crop time.*—Approximately 8–10 weeks in a 10 cm pot.

*Habit of growth.*—Compact. Freely branching. One or two pinches improve basal branching.

*Form.*—Upright, mounded.

*Size.*—Height from soil level to top of plant plane: Approximately 22.3 cm. Height of foliage only: Approximately 12.1 cm. Width (area of spread): Approximately 36 cm. Width (area of spread) of foliage only: 25.4 cm.

*Branch description.*—Quantity per plant: Approximately 6. Strength: Strong. Length from soil level to tip: Approximately 7.3 cm. Diameter: Approximately 2.9 mm. Texture: Strigose. Color: 144A. Internode length at middle of branch: Approximately 2.1 cm.

*Foliage description.*—Quantity per branch: Approximately 9. Type: Simple. Fragrance: None. Arrangement: Opposite. Aspect: At an acute angle to the stem. Shape: Elliptic. Margin: Entire. Apex: Cuspidate. Base: Sessile, clasping. Venation pattern: Pinnate. Length: Approximately 4.2 cm. Width: Approximately 1.8 cm. Texture: Upper and lower surfaces are strigose. Color of mature foliage: Upper surface: 137A with venation of 146D. Lower surface: 146A with venation of 146D.

Flowering description:

*Time to first flower.*—Approximately 8 weeks from planting of rooted cutting.

*Flowering habit.*—Freely flowering under outdoor growing conditions with substantially continuous blooming from spring through autumn and year round in greenhouse environment.

Inflorescence description:

*Appearance.*—Solitary, composite. Not persistent. Shape: Round. Aspect: Slightly cupped. Disc and ray florets develop acropetally on a capitulum. Fragrance: None.

*Lastingness of inflorescence.*—Approximately 7–10 days.

*Quantity of flowers and buds per lateral branch.*—Approximately 10 inflorescences and 12 buds.

*Size.*—Diameter: Approximately 3.6 cm. Depth: Approximately 1.5 cm.

*Bud.*—Shape: Ovate. Diameter: Approximately 7 mm. Depth: Approximately 1.4 cm. Color of sepals: 138A at apex, 143C at base. Color of petals: Closest to 93D.

*Ray florets.*—Quantity per inflorescence: Approximately 13, arranged in a single whorl. Aspect: Flat to slightly concave, facing upward. Arrangement: Very slightly overlapping at base. Shape: Ligulate. Margin: Entire. Apex: Emarginate with three tips. Base: Attenuate and fused to form tube. Length: Approximately 1.6 cm. Width: Approximately 4 mm. Texture: Glabrous with ridges. Color of young and mature ray florets: Upper surface: Between 94D and 95D. Lower surface: 92C. Tube length: 4.7 mm. Tube texture: Puberulent. Tube color: 145B.

*Disc.*—Diameter: Approximately 8.2 mm. Depth: Approximately 6 mm.

*Disc florets.*—Quantity per inflorescence: Approximately 83. Shape: Tubular with five lobes each having an acute apex. Margin: Entire. Length: Approximately 8.5 mm. Diameter at apex: Approximately 1.6 mm. Diameter at base: Approximately 1.3 mm. Texture: Glabrous. Pappus consists of many bristles, approximately 4 mm in length. Color of immature floret: 7C. Color of mature floret: 5C. Calyx shape: Cup. Calyx length: Approximately 9.5 mm. Calyx diameter: Approximately 6 mm. Texture of outer surface of calyx: Strigose. Texture of inner surface of calyx: Glabrous. Calyx color: 155A.

*Receptical.*—Diameter: 5 mm. Depth: 4 mm. Color: 145C.

*Phyllaries.*—Quantity per inflorescence: Approximately 13. Arrangement: Imbricate, arranged in several rows. Shape: Linear. Margin: Entire. Apex: Acute. Base: Truncate. Length: Approximately 1 cm. Width: Approximately 1.3 mm. Texture of outer/lower surface: Strigose. Texture of inner/upper surface: Glabrous. Color of upper surface: Closest to 143C. Color of lower surface: Closest to 143B.

*Peduncle.*—Strength: Moderate. Aspect: Erect to acute. Length: Approximately 14.8 cm. Diameter: Approximately 1.1 mm. Texture: Strigose. Color: 144B.

*Reproductive organs.*—Androecium: Present on disc florets only. Stamens: 4. Anther length: 0.6 mm. Anther color: 6C. Amount of pollen: Moderate. Pollen color: 9B. Gynoecium: Present on ray and disc florets. There is one pistil per floret. Pistil length: 9 mm. Stigma shape: Linear. Stigma length: 1.6 mm. Stigma color: 13C. Style length: 5 mm. Style color: 150C. Ovary diameter: 2 mm. Ovary color: 150D.

Seed and fruit production: Neither seed not fruit production has been observed.

Disease and pest resistance: Resistance to pathogens and pests common to *Felicia* has not been observed.

What is claimed is:

1. A new and distinct cultivar of *Felicia* plant named 'Balpinperi', substantially as herein shown and described.

* * * * *